United States Patent [19]
Fjerdingstad

[11] Patent Number: 5,370,005
[45] Date of Patent: Dec. 6, 1994

[54] METHOD AND A SAMPLING ASSEMBLY FOR TAKING A REPRESENTATIVE FLUID SAMPLE FROM A PRESSURIZED FLUID SYSTEM

[76] Inventor: Solve Fjerdingstad, Ellingsrudlia 14, N-1400 Ski, Norway

[21] Appl. No.: 50,001
[22] PCT Filed: Sep. 13, 1991
[86] PCT No.: PCT/NO91/00116
   § 371 Date: Apr. 21, 1993
   § 102(e) Date: Apr. 21, 1993
[87] PCT Pub. No.: WO92/05420
   PCT Pub. Date: Apr. 2, 1992

[30] Foreign Application Priority Data
   Sep. 14, 1990 [NO] Norway .................. 904021

[51] Int. Cl.5 .................................. G01N 1/00
[52] U.S. Cl. ..................................... 73/863.71
[58] Field of Search .......... 73/863.71, 863.81, 863.83, 73/863.85, 863.86, 864.33, 864.34

[56] References Cited
U.S. PATENT DOCUMENTS

| | | | |
|---|---|---|---|
| 3,798,972 | 3/1974 | Collins, Jr. | 73/863.71 |
| 4,683,761 | 8/1987 | Stock | 73/864.34 |
| 4,744,256 | 5/1988 | Niskin | 73/864.66 |

FOREIGN PATENT DOCUMENTS

| | | |
|---|---|---|
| 3927020 | 5/1990 | Germany . |
| 2222675 | 3/1990 | United Kingdom . |
| 2011525 | 7/1992 | WIPO ............... 73/863.71 |

Primary Examiner—Robert Raevis
Attorney, Agent, or Firm—Wenderoth, Lind & Ponack

[57] ABSTRACT

In order to allow verification of the purity of a fluid sample from a pressurized fluid system, a sampling assembly includes a pressure chamber adapted to removably receive a sampling container. An inlet in the pressure chamber of the sampling assembly is connected to a bleed point of the pressurized fluid system of which the fluid is to be sampled, and the fluid in the system is caused to flow for a predetermined time interval through the sampling container in the pressure chamber. An outlet of the sampling assembly is connected to a return point of the fluid system. When the sampling assembly is disconnected from the fluid system, the pressure in the pressure chamber is released and the sampling container now containing a representative sample of the fluid in the system may be removed from the sampling assembly for analysis of its contents.

18 Claims, 2 Drawing Sheets

METHOD AND A SAMPLING ASSEMBLY FOR TAKING A REPRESENTATIVE FLUID SAMPLE FROM A PRESSURIZED FLUID SYSTEM

BACKGROUND OF THE INVENTION

A problem encountered in connection with the collection and purity control of samples from pressurized liquid systems, such as hydraulic and central lubricating systems, is to obtain representative samples for verifying the particle purity of a sample in a particle counter or microscope. Frequently the sampling bleed orifice and valves have to be purged for a considerable time before the sample is representative. Also, current methods frequently cause considerable oil spillage since, in order to be representative, a sample requires up to half an hour of purging through the sampling bleed orifice. Further, during opening and closing of sampling bleed valves on the pressure side of the liquid system, the sample is contaminated by particles liberated in such valves.

DE 3 927 020 A1 discloses a rather complicated sampling device for taking samples of toxic or noxious fluids in a circulation system. The sampler includes a sampling container which may be of a pressure resistent type if the fluid is under pressure in the circulation system. The fluid may be caused to flow from the circulation system into the sampler via a bleed valve to be closed when the sampler has been filled as desired. Since the opening as well as the closing of the bleed valve will result in microscopic extraneous matter entrained in the fluid flowing into the sampler, this prior device would be entirely impracticable in verifying the purity of the liquid circulating in the system. Furthermore, a pressure resistant container would be expensive.

Also exemplary of the prior art is GB-2 222 675 A disclosing a relatively complex device for taking samples of a radioactive flowing liquid. The liquid is discharged into a sampling flask by utilizing the venturi effect, and the discharge ceases automatically when the sampling flask is removed from the flow system. However, the device cannot be used on pressurized fluids.

SUMMARY OF THE INVENTION

The object of the present invention is to solve the problem of how to provide a fluid sample from a system of pressurized fluid in such a manner that the sample is practically 100% representative, as to purity, of the fluid in the system.

This object is achieved through a method and a sampling assembly as defined below. Thus, the invention eliminates the risk of contamination of the fluid sample as a result of the sampling operation itself. In, the invention permits the use of inexpensive standard glass or plastics bottles for containing the sample, even when the fluid in the fluid system is working under high pressures.

The invention is applicable to all types of pressurized fluid systems, but is primarily intended for lubricating oil systems in connection with heavy machinery in processing industries, rolling mills, bearings for rolls in paper mills and shafts in ship propulsion plants, important hydraulic plants etc. Although the invention is primarily intended for taking liquid samples it may just as well be applied to gases.

BRIEF DESCRIPTION OF THE DRAWINGS

The invention is described below with reference to the drawings in which.

DETAILED DESCRIPTION OF THE INVENTION

Figure 2:
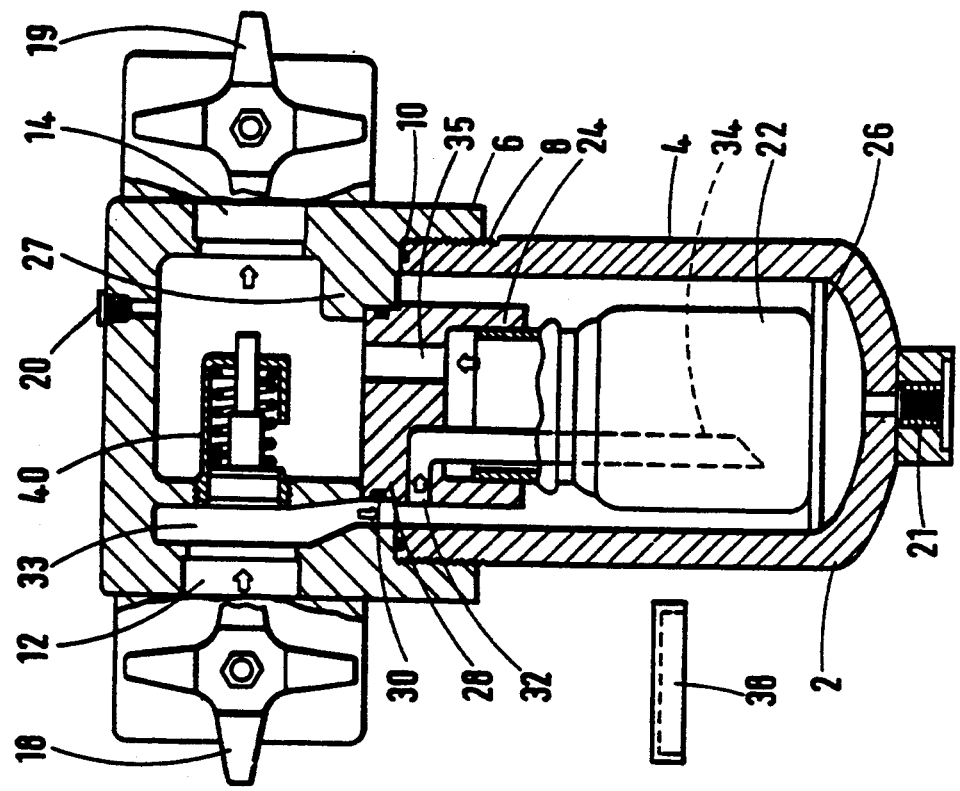
FIG. 2 is a longitudinal section taken along line II—II in FIG. 1

In the drawings reference numeral 1 generally denotes a sampler or sampling assembly associated with a circulating pressurized fluid system S the fluid of which is to be controlled. For example, the fluid could be the oil in a machinery pressurized lubricating system. The assembly 1 comprises a pressure chamber 2 designed to resist a pressure at least as high as the pressure of the fluid system S. In the example shown pressure chamber 2 consists of a cylindrical lower body 4 releasably and sealingly connected to an upper body 6, e.g. by means of threads 8 and sealing ring 10. The upper body 6 is provided with an inlet 12 and outlet 14 each connected to a respective coupling member 16a, preferably of the rapid coupling type. Further, the inlet 12 and outlet 14 each communicates with a manually activated flow control valve 18 and 19 respectively. A closable vent 20 is provided at the top of the chamber 2 upper body 6 and a closable drain 21 is provided in the bottom of the chamber lower body 4.

The pressure chamber 2 is constructed to house a sampling container 22, e.g. in the form of a glass bottle having a removable cap 24, e.g. made from hard plastics. The bottle 22 rests on a support 26 in the chamber lower body 4, and a top portion 28 of the cap 24, including a seal ring 30, is sealingly received in an annular recess in a reduced diameter portion 27 of the chamber upper body 6.

The bottle cap 24 is provided with a substantially horizontal entrance 32 one side of which communicates, via a passage 33 through the reduced diameter portion 27 of the pressure chamber upper body 6, with the pressure chamber inlet 12, and the other side of which communicates with a dip tube 34 depending towards the bottom of the sampling bottle 22. A vertical passage 35 through the bottle cap 24 forms an exit from the bottle 22.

Optionally, a spring-biased normally closed bypass valve 40 may be installed in the pressure chamber 2 between its inlet 12 and outlet 14.

The above described sampler 1 operates essentially in the following manner.

With closed inlet and outlet valves 18, 19 and closed vent and drain openings 20, 21 the two coupling members 16a of the sampling assembly 1 are connected to mating coupling members 16b provided at a bleed point A and a return point B, respectively, in the pressure fluid system S. The inlet valve 18 is gradually opened while vent 20 is also opened. Fluid from the system S to be controlled then flows via bleed point A and inlet 12 into the pressure chamber 2 filling the latter, including the sampling bottle 22, as the air present in the chamber evacuates through vent 20. Once all of the air is evacuated vent 20 is closed. When the outlet valve 19 is now opened, liquid from the system S will flow through the sampling assembly 1 as indicated by arrows in FIG. 2: from the pressure chamber inlet 12 along the passage 33 in chamber upper body 6, into the entrance 32 of the bottle cap 24 and down through the dip tube 34 to the bottom of bottle 22, out of the bottle through exit passage 35 in the bottle cap, and out through chamber outlet 14 back to the pressure liquid system S through return point B. The valves 18, 19 are of the type in which the flow rate of the fluid continuously flowing through the sampling assembly can be adjusted from zero (closed valve) to a predetermined maximum value, by appropriate setting of either one of these valves, preferably the outlet valve 19.

The sampling assembly 1 may be connected in series with the flow circuit of the liquid system S, i.e. the entire circulation liquid flow passes through the sampler; or it may be connected in parallel such that only a partial flow passes through the sampler. The bypass valve 40 is important, particularly in the first mentioned series coupling alternative, if the cross section or capacity of the sampling bottle 22 is insufficient to cope with the entire fluid flow through the chamber inlet 12, since it permits part of the main fluid flow to pass through the sampler and back into the system. The flow rate of such partial flow will depend on the biasing force of the bypass valve spring. Alternatively, valve 40 or a similar bypass could be provided between bleed point A and return point B in system S rather than in sampler 1.

The fluid is allowed to circulate through the sampling bottle 22 for at least 15 to 20 minutes to make certain that the fluid flowing therethrough will be representative of the system liquid, whereupon the outlet valve 19 is closed to stop the above described fluid circulation through the sampler 1. Then, after having closed the outlet valve 19, also the inlet valve 18 of the pressure chamber 2 is closed.

By closing the outlet valve 19 prior to closing the inlet valve 18, the liquid sample contained in the bottle 2 during the operation of closing the inlet valve 18 will only be subject to a static pressure and therefore such sample will not be contaminated by particles that would detach from the inlet valve had the valves been closed in the opposite sequence.

Pressure in the sampler 1 is then released by opening the vent 20. Then drain 21 is opened to empty the fluid present in the pressure chamber 2 (if it is a liquid), leaving the fluid in the sampling bottle 22 below its entrance 32.

Now the lower body 4 of the pressure chamber 2 can be unscrewed from the upper body 6 and the sampling bottle 22 lifted out of the chamber lower body after having placed a plastic lid 38 or the like over the bottle cap top portion 28 and closed its entrance 32 by means of a plug or the like (not shown) to thereby close the bottle which may then be sent to the laboratory for controlling the fluid sample confined therein. Finally, sampler 1 can be uncoupled from the system points A, B if desired.

Figure 1:
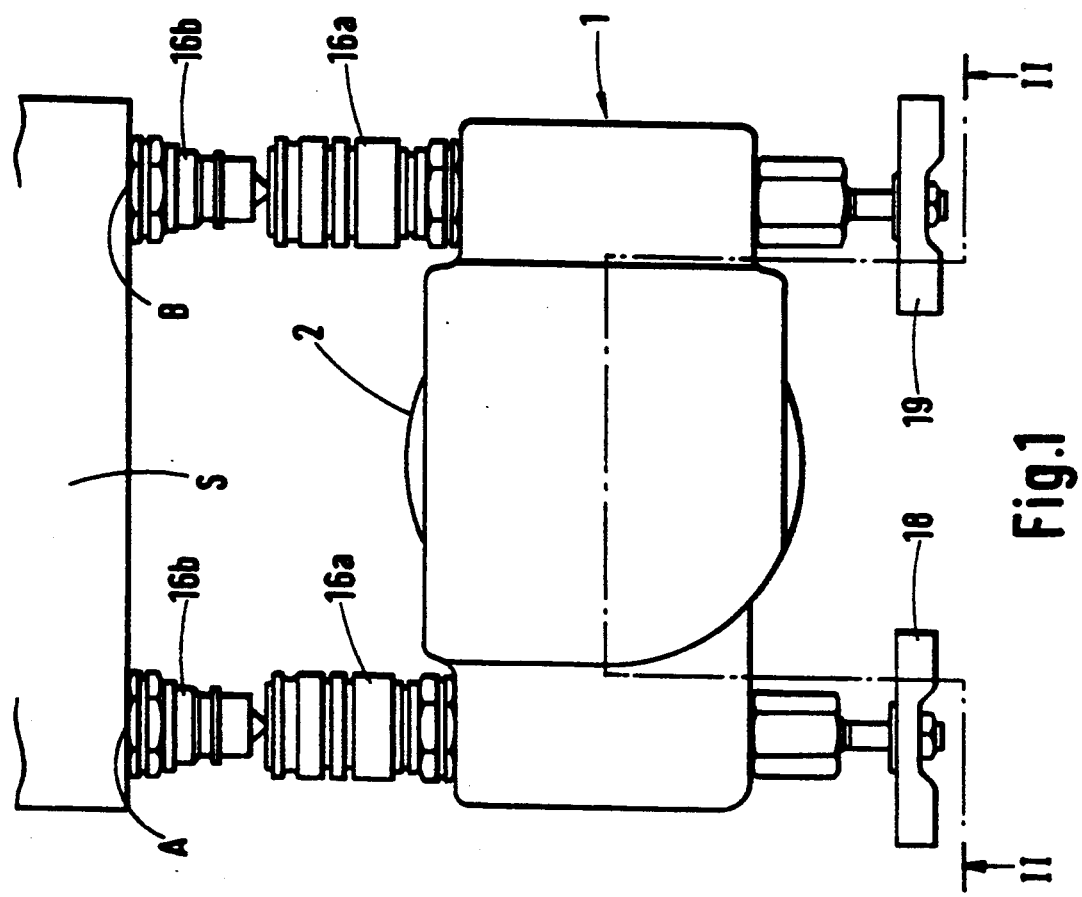
FIG. 1 is a plan view of a possible embodiment of a sampling assembly according to the invention.
Figure 3:
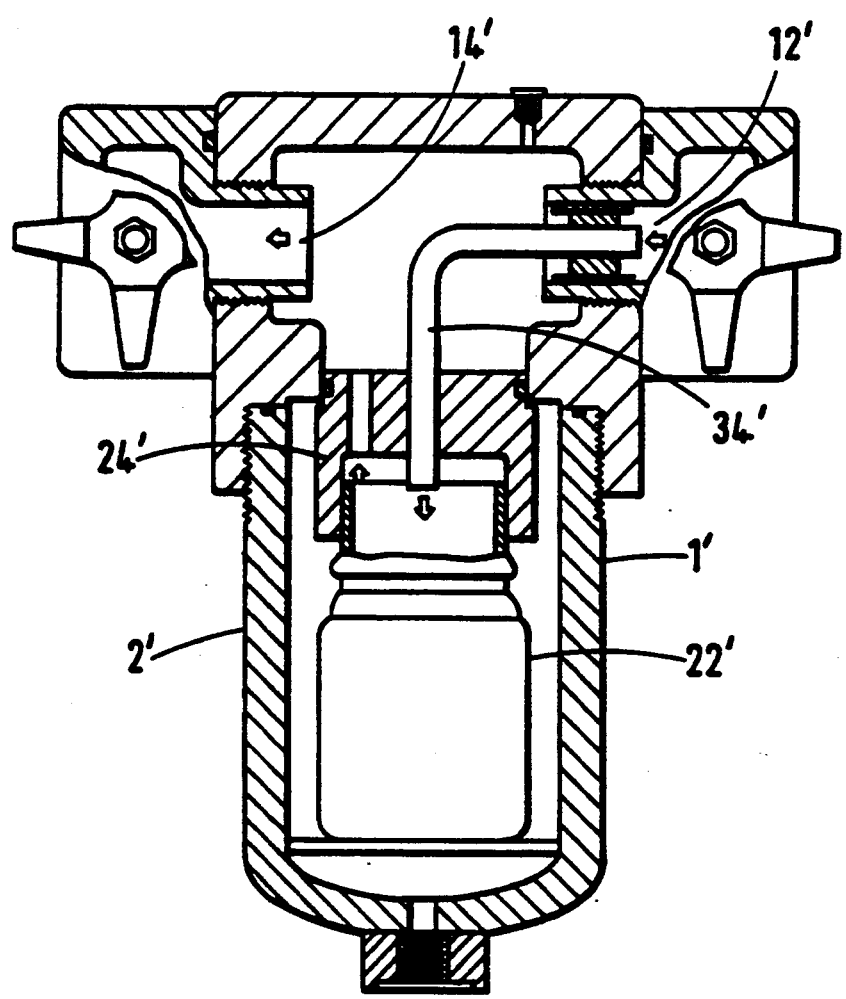
FIG. 3 is a section similar to FIG. 2 but illustrating a somewhat modified embodiment.

If the sampler 1 is to be connected in series with the liquid system S, then the modified embodiment 1' shown in FIG. 3 might be advantageous. Here the bypass valve 4 of the embodiment according to FIG. 2 is omitted and the dip tube 34 of the latter embodiment is replaced by a pitot tube 34', one leg of which is positioned directly in the fluid flow path between inlet 12' and outlet 14' of pressure chamber 2', other leg thereof extending down into sampling bottle 22' through a vertical entrance in bottle cap 24'. The remainder of the design and operation of the sampler 1' is essentially similar to that of the preceding sampler according to FIGS. 1 and 2.

Although the samplers in the above, embodiments are adapted to be removably connected to the liquid system to be controlled, the sampler may advantageously be permanently connected thereto, e.g. in case the fluid system is a machinery lubricating oil system. This would allow maintainence inspectors to collect samples from several machines during routine inspection rounds.

The sampler 1 according to the invention has been tested in hydraulic systems with pressure peaks up to 350 bar with a glass bottle in the pressure chamber. During such tests there were no signs that the glass bottles did not resist the load from the pressure in the system.

Of course the sampling bottle 22 need not be shaped and supported exactly as described above and illustrated in the drawings, and similarly the pressure chamber 2 need not be designed in exact conformence with the given examples, since a person skilled in the art easily may recognize larger or smaller design modifications without departing from the inventive idea. The essential feature is that the sampler 1 is constructed in such a way that the pressure fluid to be controlled is allowed to flow through the sampling container in the pressure chamber for a predetermined time interval and the container then is removed from the sampler in a simple manner.

The invention is particularly intended to be used on flowing pressurized fluid systems, but it may also be used in connection with static pressurized fluid systems, the inlet end of the sampler in that case being connected to a bleed point in the fluid system while the outlet thereof discharges into a container or the like with a lower pressure than that of the pressure chamber.

I claim:

1. A method for taking a representative fluid sample from a pressurized fluid system, said method comprising:
   providing a pressure chamber having an inlet connectable on a first side thereof through an inlet valve to a bleed point of said fluid system and an outlet connected on a first side thereof to an outlet valve;
   providing a sampling container having an entrance and an exit;
   detachably mounting said sampling container within said pressure chamber such that said entrance communicates with a second side of said inlet and said exit communicates with a second side of said outlet;
   opening said inlet valve and said outlet valve such that pressurized fluid flows from said bleed point of said fluid system through said sampling container and out said outlet valve;
   closing said outlet valve to interrupt said flow through said sampling container, and then closing said inlet valve to retain a fluid sample in said sampling container; and
   removing said sampling container and fluid sample from said pressure chamber.

2. A method as claimed in claim 1, wherein said outlet valve is connected to said fluid system, and said flow of fluid out of said outlet valve is returned to said fluid system.

3. A method as claimed in claim 2, wherein said fluid flow is returned to said fluid system at a return point thereof separate from said bleed point.

4. A method as claimed in claim 1, wherein said flow of said fluid out of said outlet valve is discharged therefrom at a pressure lower than that of said pressure chamber.

5. A method as claimed in claim 1, comprising providing said sampling container with a vent, and said opening comprises opening said inlet valve before said outlet valve and venting air in said sampling container through said vent.

6. A method as claimed in claim 1, comprising providing said entrance and said exit of said sampling container in a top cap of said sampling container.

7. A sampling assembly for obtaining a representative fluid sample from a pressurized fluid system, said assembly comprising:
an inlet valve to be connected to a bleed point of the fluid system and an outlet valve;
a pressure chamber comprising an upper body and a lower body detachably sealingly connected to said upper body, said upper body having formed therein an inlet connected on a first side thereof to said inlet valve and an outlet connected on a first side thereof to said outlet valve;
a sampling container having a top cap having an entrance and an exit of said sampling container; and
said sampling container being detachable mountable within said pressure chamber in a position such that said entrance communicates with a second side of said inlet and said exit communicates with a second side of said outlet;
whereby opening of said inlet valve and said outlet valve will cause pressurized fluid to flow from the fluid system through said sampling container, after which selected closing of said outlet valve and said inlet valve will retain a fluid sample in said sampling container, whereafter said sampling container and the thus retained fluid sample may be removed from said pressure chamber.

8. An assembly as claimed in claim 7, wherein said inlet valve and said outlet valve are mounted on said pressure chamber.

9. An assembly as claimed in claim 7, wherein said outlet valve is connectable to a return point of the fluid system.

10. An assembly as claimed in claim 7, wherein said sampling container comprises a glass bottle.

11. An assembly as claimed in claim 7, further comprising a dip tube connected to said entrance and extending to the bottom of said sampling container.

12. An assembly as claimed in claim 7, further comprising a pitot tube having a first leg positioned in a path of fluid flow between said inlet and said outlet of said pressure chamber and a second leg connected to said entrance of said sampling container.

13. An assembly as claimed in claim 7, wherein said lower body carries said sampling container.

14. An assembly as claimed in claim 7, wherein said lower body comprises a substantially cylindrical member having an open top sealed to an open bottom portion of said upper body.

15. An assembly as claimed in claim 14, wherein said cylindrical member is threaded to said upper body.

16. An assembly as claimed in claim 7, wherein said upper body has a vent, and said lower body has a drain.

17. An assembly as claimed in claim 7, further comprising a bypass valve positioned adjacent said inlet.

18. An assembly as claimed in claim 17, wherein said bypass valve is normally closed and opens to allow fluid flow from said inlet to bypass said sampling container and to pass directly to said outlet.

* * * * *